United States Patent
Aoki et al.

(10) Patent No.: US 10,233,402 B2
(45) Date of Patent: Mar. 19, 2019

(54) PRESSURE MEDIUM OIL AND METHOD FOR USING SAID PRESSURE MEDIUM OIL

(71) Applicant: IDEMITSU KOSAN CO., LTD., Chiyoda-ku (JP)

(72) Inventors: Shinji Aoki, Ichihara (JP); Masahiro Kobessho, Ichihara (JP); Keizo Murata, Osaka (JP)

(73) Assignee: IDEMITSU KOSAN CO., LTD., Chiyoda-ku (JP)

( * ) Notice: Subject to any disclaimer, the term of this patent is extended or adjusted under 35 U.S.C. 154(b) by 0 days.

(21) Appl. No.: 15/508,128

(22) PCT Filed: Sep. 11, 2015

(86) PCT No.: PCT/JP2015/075929
§ 371 (c)(1),
(2) Date: Mar. 2, 2017

(87) PCT Pub. No.: WO2016/039468
PCT Pub. Date: Mar. 17, 2016

(65) Prior Publication Data
US 2017/0283730 A1    Oct. 5, 2017

(30) Foreign Application Priority Data
Sep. 12, 2014  (JP) .................. 2014-186256

(51) Int. Cl.
*C07F 7/22*   (2006.01)
*C07F 7/24*   (2006.01)
*C07F 7/30*   (2006.01)
*C10M 105/80* (2006.01)

(52) U.S. Cl.
CPC ........ *C10M 105/80* (2013.01); *C07F 7/2208* (2013.01); *C07F 7/24* (2013.01); *C07F 7/30* (2013.01); *C10M 2227/08* (2013.01); *C10M 2227/082* (2013.01); *C10M 2227/083* (2013.01); *C10N 2240/20* (2013.01)

(58) Field of Classification Search
CPC ............ C10M 105/80; C10M 2227/06; C10M 2227/082; C10M 2227/083; C07F 7/2208; C07F 7/24; C07F 7/30
See application file for complete search history.

(56) References Cited

U.S. PATENT DOCUMENTS

| | | | | |
|---|---|---|---|---|
| 2,975,137 A | * | 3/1961 | Stuart | C09K 5/044 252/68 |
| 2,994,189 A | * | 8/1961 | Rex | C06B 43/00 149/74 |
| 3,510,502 A | * | 5/1970 | Moedritzer | C07F 7/0836 252/74 |
| 3,725,338 A | * | 4/1973 | Weisfeld | C08K 5/175 524/178 |
| 4,163,731 A | | 8/1979 | Randell et al. | |
| 4,257,902 A | | 3/1981 | Singer | |
| 5,095,165 A | | 3/1992 | Chen | |
| 5,268,522 A | * | 12/1993 | Bournonville | C07C 2/00 585/407 |
| 2003/0134967 A1 | * | 7/2003 | Hukkanen | C10M 173/02 524/556 |

FOREIGN PATENT DOCUMENTS

| | | |
|---|---|---|
| EP | 0 582 131 A1 | 2/1994 |
| JP | 53-20067 A | 2/1978 |
| JP | 53-55489 A | 5/1978 |
| JP | 2011-132285 A | 7/2011 |
| JP | 2011132285 A * | 7/2011 |
| WO | 2007/058064 A1 | 5/2007 |
| WO | 2008/108356 A1 | 9/2008 |

OTHER PUBLICATIONS

International Search Report dated Oct. 20, 2015 in PCT/JP2015/075929 filed Sep. 11, 2015.
J. Jerome et al., "Superconductivity in a synthetic organic conductor $(TMTSF)_2PF_6$", J. Physique—Lettres, Vo. 41, Feb. 15, 1980, pp. L-95-L-98.
Keizo Murata et al., "Pressure Phase Diagram of the Organic Superconductor $\beta$-$(BEDT-TTF)_2I_3$", Journal of the Physical Society of Japan, vol. 54, No. 6, Jun. 1985, pp. 2084-2087.
Hiromi Taniguchi et al., "Superconductivity at 14.2 K in Layered Organics under Extreme Pressure", Journal of the Physical Society of Japan, vol. 72, No. 3, Mar. 2003, pp. 468-471.
Extended European Search Report dated Mar. 22, 2018 in corresponding European Patent Application No. 15840956.5, 8 pages.
"Database accession No. 105:46108", Chemical Abstracts Service, XP002778860, 1984, 1 page.
Office Acton dated Jan. 8, 2019 in Japanese Patent Application No. 2016-547810 (with English translation), filed Sep. 11, 2015.

* cited by examiner

Primary Examiner — James C Goloboy
(74) Attorney, Agent, or Firm — Oblon, McClelland, Maier & Neustadt, L.L.P.

(57) ABSTRACT

Provided are a pressure medium oil, containing a Group-14 element-containing organic compound selected from an organic germanium compound, an organic tin compound, and an organic lead compound, and a method for using a pressure medium oil, which includes applying a pressure to a substance via the pressure medium oil. The pressure medium oil does not solidify even under an ultrahigh pressure of more than 3.7 GPa at room temperature (25° C.) and has a low pour point, and hardly dissolves a conductive paste.

17 Claims, No Drawings

PRESSURE MEDIUM OIL AND METHOD FOR USING SAID PRESSURE MEDIUM OIL

CROSS-REFERENCE TO RELATED APPLICATIONS

This application is a National Stage of PCT/JP2015/075929, which was filed on Sep. 11, 2015. This application is based upon and claims the benefit of priority to Japanese Application No. 2014-186256, which was filed on Sep. 12, 2014.

TECHNICAL FIELD

The present invention relates to a pressure medium oil, and a method for using the pressure medium oil.

BACKGROUND ART

Studies to find out new functions of a substance through application of ultra-high pressure thereto have been widely carried out around the world.

For example, an organic superconductor $(TMTSF)_2PF_6$ was found on the basis of studies on the pressure-dependency of metal-nonmetal transition, and an 8K superconductor $\beta\text{-}(BEDT\text{-}TTF)_2I_3$ was found through studies on the pressure-dependency of characteristics of the substance (for example, see NPLs 1 and 2).

Novel superconductors of these substances expressed the characteristic of superconductivity under 1 GPa or less, but a superconductor of $\beta'\text{-}(BEDT\text{-}TTF)_2ICl_2$ was found under a high pressure of 8 GPa, and showed a transition temperature of 14 K that is the highest among organic conductors (for example, see NPL 3).

Development of new substances has been carried out through investigation and resolution of change in physical properties by pressure change with respect to not only such organic superconductors but also solid substances such as oxide conductors and the like.

In general, as a means for applying an ultrahigh pressure to a substance the substance must be pressurized gently and uniformly, and therefore in many cases, the object substance is given a pressure via a pressure medium oil that is a liquid pressure medium.

Regarding the characteristics that are required for the pressure medium oil for measurement under high pressure as mentioned above, the first is that the pressure medium oil does not solidify throughout a broad pressure range and can maintain a liquid state. In other words, when a pressure medium oil solidifies during pressure application, it provides monoaxial compression and fails in uniform compression.

Next, in the case of electric conductivity measurement under pressure, a conductive paste is often used as an electrode, and a pressure medium oil is required to have a characteristic of not dissolving the conductive paste.

Further, when cooled down to be at a temperature not higher than room temperature, a pressure medium oil solidifies at such a low temperature even though it is liquid during pressurization. When a great pressure change occurs during solidification, a brittle sample may be broken. Accordingly, it is further desired that a pressure medium oil has a low pour point as another characteristic.

As still other necessary characteristics thereof, it is also desired that a pressure medium oil has a small compressibility in order that a wall does not contact with a sample during compression.

In the case where a sample of a porous substance such as zeolite is analyzed for pressure effect thereto, it is desired that a pressure medium oil does not come in the space of the pores of the porous substance. It has been verified that helium, and a mixed liquid of methanol and ethanol has extremely good hydrostatic pressure performance, but the molecular size of these substances is smaller than the pore size of a porous substance, and it is often difficult to investigate the pressure characteristics of a porous substance. Accordingly, it is desired that the molecular size of a pressure medium oil is large than the pore size of a porous substance.

Various developments have been made regarding pressure medium oils capable of satisfying these required characteristics.

For example, PTL 1 discloses an invention relating to a pressure medium oil of a hydrocarbon compound and/or an ether compound whose kinematic viscosity at 40° C., viscosity index, density, and pour point each fall within a specific range. PTL 1 says that the solidification pressure at room temperature of the pressure medium oil reached 2.7 GPa.

PTL 2 discloses an invention relating to a pressure medium oil of a silicon-containing organic compound whose kinematic viscosity at 40° C., viscosity index, and pour point each fall within a specific range. PTL 2 says that the solidification pressure at room temperature of the pressure medium oil reached 3.7 GPa.

CITATION LIST

Patent Literature

PTL 1: WO2007/058064
PTL 2: WO2008/108356

Non Patent Literature

NPL 1: J. Physique Lett. vol. 41 (1980) 95.
NPL 2: Journal of Physical Society of Japan, vol. 54 (1985) 2084.
NPL 3: Journal of Physical Society of Japan, vol. 72 (2003) 468.

SUMMARY OF INVENTION

Technical Problem

The pressure medium oils disclosed in PTLs 1 and 2 have a high solidification pressure at room temperature, but a pressure medium oil having a further higher solidification pressure and realizing a higher performance is desired.

The present invention has been made in consideration of the above-mentioned situation, and its object is to provide a pressure medium oil which does not solidify even under an ultrahigh pressure higher than 3.7 GPa at room temperature (25° C.), has a low pour point, and hardly dissolves a conductive paste, and to provide a method for using the pressure medium oil.

Solution to Problem

As a result of assiduous studies, the present inventors have found that a pressure medium oil containing a specific Group-14 element-containing organic compound can solve the above-mentioned problems and have completed the present invention.

Specifically, the present invention provides the following [1] to [3].

[1] A pressure medium oil containing a Group-14 element-containing organic compound selected from an organic germanium compound, an organic tin compound, and an organic lead compound.
[2] A pressure medium oil containing an organic germanium compound.
[3] A method for using a pressure medium oil, which includes applying a pressure to a substance via the pressure medium oil of the above [1] or [2].

Advantageous Effects of Invention

The pressure medium oil of the present invention has characteristics of not solidifying even under an ultrahigh pressure higher than 3.7 GPa at room temperature (25° C.), having a low pour point, and hardly dissolving a conductive paste, and realizes uniform pressure application of higher than 3.7 GPa to an object substance to be pressurized.

DESCRIPTION OF EMBODIMENTS

[Pressure Medium Oil]

The pressure medium oil (1) of the present invention contains a Group-14 element-containing organic compound selected from an organic germanium compound, an organic tin compound, and an organic lead compound. The pressure medium oil (1) of the present invention may be a pressure medium oil that contains, as a Group-14 element-containing organic compound, only one Group-14 element-containing organic compound selected from an organic germanium compound, an organic tin compound, and an organic lead compound, or may also be a pressure medium oil that contains two or more of Group-14 element-containing organic compounds selected from an organic germanium compound, an organic tin compound, and an organic lead compound.

The pressure medium oil (2) of another aspect of the present invention contains an organic germanium compound.

Hereinunder, the pressure medium oils (1) and (2) of the present invention are collectively referred to as the pressure medium oil of the present invention.

The pressure medium oil of one embodiment of the present invention may contain, within a range not detracting from the effects of the present invention, various additives along with the above-mentioned Group-14 element-containing organic compound.

The content of the Group-14 element-containing organic compound to be contained in the pressure medium oil of one embodiment of the present invention is, from the viewpoint of realizing a pressure medium oil having a high solidification pressure at room temperature (25° C.), preferably from 70 to 100% by mass, based on the total amount (100% by mass) of the pressure medium oil, more preferably from 80 to 100% by mass, even more preferably from 85 to 100% by mass, further more preferably from 90 to 100% by mass, even further more preferably from 95 to 100% by mass.

The organic germanium compound that is used as a Group-14 element-containing organic compound in the present invention may be any compound at least containing a germanium atom, a carbon atom, and a hydrogen atom, the organic tin compound may be any compound at least containing a tin atom, a carbon atom, and a hydrogen atom, and the organic lead compound may be any compound containing at least a lead atom, a carbon atom, and a hydrogen atom.

The organic germanium compound, the organic tin compound, and the organic lead compound falling within the range of the Group-14 element-containing organic compound for use in one embodiment of the present invention may also be compounds further containing one or more selected from a nitrogen atom, an oxygen atom, a sulfur atom, and a halogen atom (fluorine atom, chlorine atom, bromine atom, iodine atom) and the like, in addition to the above-mentioned atoms (germanium atom, tin atom, lead atom, carbon atom, and hydrogen atom).

The pressure medium oil of the present invention contains a Group-14 element-containing organic compound selected from an organic germanium compound, an organic tin compound, and an organic lead compound, and therefore can be a pressure medium oil having such characteristics that it does not solidify even under an ultrahigh pressure higher than 3.7 GPa at room temperature (25° C.), it has a low pour point, and it hardly dissolves a conductive paste.

The kinematic viscosity at 40° C. of the Group-14 element-containing organic compound for use in one embodiment of the present invention is preferably 20 mm$^2$/s or less, more preferably from 1.0 to 15 mm$^2$/s, even more preferably from 1.5 to 12 mm$^2$/s.

When the kinematic viscosity is 20 mm$^2$/s or less, a phenomenon of lowering the solidification pressure at room temperature (25° C.) can be prevented. On the other hand, when the kinematic viscosity is 1.0 mm$^2$/s or more, loss by evaporation of the pressure medium oil and troubles such as combustion risk can be prevented.

The kinematic viscosity at 100° C. of the Group-14 element-containing organic compound for use in one embodiment of the present invention is preferably from 0.1 to 15 mm$^2$/s, more preferably from 0.3 to 10 mm$^2$/s, even more preferably from 0.5 to 7 mm$^2$/s.

In the present invention, the kinematic viscosity at 40° C. or 100° C. means a value measured according to the method of JIS K 2283, and the same shall apply to the kinematic viscosity to be described hereinunder.

The pour point of the Group-14 element-containing organic compound for use in one embodiment of the present invention is, from the viewpoint of realizing a pressure medium oil that does not solidify even at a low temperature and can be used even in low-temperature experiments, preferably −40° C. or lower, more preferably −45° C. or lower, even more preferably lower than −50° C.

In the present invention, the pour point means a value measured according to the method of JIS K 2269, and the same shall apply to the pour point to be described hereinunder.

The organic germanium compound that is used as a Group-14 element-containing organic compound in one embodiment of the present invention may be a divalent organic germanium compound, and may be a tetravalent organic germanium compound, but is preferably a tetravalent organic germanium compound.

Also similarly, the organic tin compound that is used as a Group-14 element-containing organic compound in one embodiment of the present invention may be a divalent organic tin compound, and may be a tetravalent organic tin compound, but is preferably a tetravalent organic tin compound.

Also similarly, the organic lead compound that is used as a Group-14 element-containing organic compound in one embodiment of the present invention may be a divalent organic lead compound, and may be a tetravalent organic lead compound, but is preferably a tetravalent organic lead compound.

From the viewpoint of realizing a pressure medium oil having a high solidification pressure at room temperature (25° C.), the Group-14 element-containing organic compound preferably contains a compound represented by the following general formula (1).

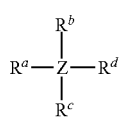

(1)

In the above general formula (1), each of $R^a$, $R^b$, $R^c$, and $R^d$ independently represents a hydrogen atom, a halogen atom, an alkyl group, or an alkoxy group, with the proviso that at least one of $R^a$, $R^b$, $R^c$, and $R^d$ is an alkyl group or an alkoxy group. Z represents a germanium atom, a tin atom or a lead atom. In other words, in the pressure medium oil (1), Z is a germanium atom, a tin atom or a lead atom. In the pressure medium oil (2), Z is a germanium atom. Each of $R^a$ to $R^d$ may be the same as or different from each other.

The carbon number of the alkyl group that can be selected for $R^a$ to $R^d$ is preferably from 1 to 30, more preferably from 2 to 20, even more preferably from 2 to 16, still more preferably from 2 to 12.

Examples of the alkyl group include a methyl group, an ethyl group, an n-propyl group, an isopropyl group, an n-butyl group, an isobutyl group, an s-butyl group, a t-butyl group, a pentyl group (including isomers), a hexyl group (including isomers), a heptyl group (including isomers), an octyl group (including isomers), a nonyl group (including isomers), a decyl group (including isomers), an undecyl group (including isomers), a dodecyl group (including isomers), a tridecyl group (including isomers), a tetradecyl group (including isomers), an octadecyl group (including isomers), an eicosyl group (including isomers), a tetracosyl group (including isomers), etc.

The alkyl group may be linear or branched.

The carbon number of the alkoxy group that can be selected for $R^a$ to $R^d$ is preferably from 1 to 30, more preferably from 2 to 20, even more preferably from 2 to 16, still more preferably from 2 to 12.

The alkoxy group includes a group represented by —OR' (R' is the above-mentioned alkyl group having 1 to 30 carbon atoms), specifically including a methoxy group, an ethoxy group, a propoxy group, a butoxy group, a pentyloxy group, a hexyloxy group, etc.

The alkoxy group may be linear or branched.

From the viewpoint of realizing a pressure medium oil having a high solidification pressure at room temperature (25° C.), it is preferable that each of $R^a$ to $R^d$ in the general formula (1) independently represents a hydrogen atom, an alkyl group having 1 to 30 carbon atoms, or an alkoxy group having 1 to 30 carbon atoms, more preferably a hydrogen atom or an alkyl group having 1 to 30 carbon atoms, and even more preferably an alkyl group having 1 to 30 carbon atoms. The preferred range of the carbon number of the alkyl group and the alkoxy group is as mentioned above.

From the viewpoint of realizing a pressure medium oil having a high solidification pressure at room temperature (25° C.), it is also preferable that the Group-14 element-containing organic compound contains a compound represented by the following general formula (2).

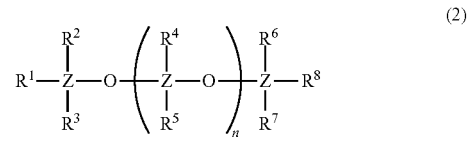

In the general formula (2), each of $R^1$ to $R^8$ independently represents a hydrogen atom, a halogen atom, an alkyl group or an alkoxy group, with the proviso that at least one of $R^1$ to $R^8$ is an alkyl group or an alkoxy group. n indicates an integer of 0 or more.

Each of Z independently represents a germanium atom, a tin atom or a lead atom, and plural Z's may be the same as or different from each other. The compound represented by the general formula (2) may be a compound having any one alone of a unit where Z is a germanium atom, a unit where Z is a tin atom, and a unit where Z is a lead atom, or may be a compound having two or more kinds of such units. In other words, in the pressure medium oil (1), the compound may have only one alone of a unit where Z is a germanium atom, a unit where Z is a tin atom, and a unit where Z is a lead atom, or may have two or more kinds of such units. In the pressure medium oil (2), the compound has a unit where Z is a germanium atom.

In the general formula (2), each of $R^1$ to $R^8$ independently represents a hydrogen atom, a halogen atom (fluorine atom, chlorine atom, bromine atom, iodine atom), an alkyl group or an alkoxy group, with the proviso that at least one of $R^1$ to $R^8$ is an alkyl group or an alkoxy group. $R^1$ to $R^8$ may be the same as or different from each other.

n indicates an integer of 0 or more, but is preferably an integer of 1 or more, more preferably an integer of 2 to 30.

For the "alkyl group" and the "alkoxy group" that can be selected for $R^1$ to $R^8$, the same as those for the "alkyl group" and the "alkoxy group" that can be selected for $R^a$ to $R^d$ in the above-mentioned general formula (1) may be mentioned.

The carbon number of the "alkyl group" and the "alkoxy group" that can be selected for $R^1$ to $R^8$ is preferably from 1 to 30, more preferably from 2 to 20, even more preferably from 2 to 16, still more preferably from 2 to 12.

From the viewpoint of realizing a pressure medium oil having a high solidification pressure at room temperature (25° C.), preferably, each of $R^1$ to $R^8$ in the general formula (2) independently represents a hydrogen atom, an alkyl group having 1 to 30 carbon atoms, or an alkoxy group having 1 to 30 carbon atoms, more preferably a hydrogen atom or an alkyl group having 1 to 30 carbon atoms, even more preferably an alkyl group having 1 to 30 carbon atoms. The preferred range of the carbon number of the alkyl group and the alkoxy group is the same as mentioned above.

In one embodiment of the present invention, the content of the compound represented by the general formula (1) or (2) is, from the viewpoint of realizing a pressure medium oil having a high solidification pressure at room temperature (25° C.), preferably from 70 to 100% by mass based on the total amount (100% by mass) of the Group-14 element-containing organic compound in the pressure medium oil, more preferably from 80 to 100% by mass, even more preferably from 90 to 100% by mass.

Taking particular note of the type of the Group-14 element-containing organic compound contained therein, the pressure medium oil of the present invention is grouped into the following embodiments.

Pressure medium oil (A) containing an organic germanium compound (hereinafter this may also be referred to as "pressure medium oil (A)").

Pressure medium oil (B) containing an organic tin compound (hereinafter this may also be referred to as "pressure medium oil (B)").

Pressure medium oil (C) containing an organic lead compound (hereinafter this may also be referred to as "pressure medium oil (C)").

It is defined that the pressure medium oil containing both an organic germanium compound and an organic tin compound belongs to both embodiments of the pressure medium oils (A) and (B).

It is defined that the pressure medium oil containing both an organic germanium compound and an organic lead compound belongs to both embodiments of the pressure medium oils (A) and (C).

It is defined that the pressure medium oil containing both an organic tin compound and an organic lead compound belongs to both embodiments of the pressure medium oils (B) and (C).

It is defined that the pressure medium oil containing all of an organic germanium compound, an organic tin compound, and an organic lead compound belongs to all the embodiments of the pressure medium oils (A), (B), and (C).

The pressure medium oils (A) to (C) that are embodiments of the present invention are described below.

[Pressure Medium Oil (A)]

The pressure medium oil (A) that is one embodiment of the present invention contains an organic germanium compound, but may further contain various additives within a range not detracting from the effects of the present invention.

In the pressure medium oil (A) that is one embodiment of the present invention, one type of organic germanium compound may be used singly, or two or more types of organic germanium compounds may be used in combination. The pressure medium oil (A) may contain, as the Group-14 element-containing organic compound therein, any other Group-14 element-containing organic compound than an organic germanium compound, but the content of the other Group-14 element-containing organic compound than the organic germanium compound is preferably not more than the content of the organic germanium compound therein.

The content of the organic germanium compound contained in the pressure medium oil (A) that is one embodiment of the present invention is, from the viewpoint of realizing a pressure medium oil having a high solidification pressure at room temperature (25° C.), preferably from 70 to 100% by mass based on the total amount (100% by mass) of the pressure medium oil (A), more preferably from 80 to 100% by mass, even more preferably from 85 to 100% by mass, still more preferably from 90 to 100% by mass, further more preferably from 95 to 100% by mass.

The organic germanium compound contained in the pressure medium oil (A) is as mentioned above, but from the viewpoint of realizing a pressure medium oil having a high solidification pressure at room temperature (25° C.), preferably, a compound represented by the following general formula (1A) is contained.

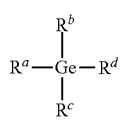

(1A)

In the general formula (1A), each of $R^a$, $R^b$, $R^c$, and $R^d$ independently represents a hydrogen atom, a halogen atom, an alkyl group or an alkoxy group, with the proviso that at least one of $R^a$, $R^b$, $R^c$, and $R^d$ is an alkyl group or an alkoxy group.

$R^a$ to $R^d$ in the general formula (1A) have the same meanings as those of $R^a$ to $R^d$ in the general formula (1), and for example, specific exemplified groups and the preferred carbon number of the selectable "alkyl group" and "alkoxy group" are the same as above.

In other words, preferably, each of $R^a$ to $R^d$ in the general formula (1A) independently represents a hydrogen atom, an alkyl group having 1 to 30 (preferably from 2 to 20, more preferably from 2 to 16, even more preferably from 2 to 12) carbon atoms, or an alkoxy group having 1 to 30 (preferably from 2 to 20, more preferably from 2 to 16, even more preferably from 2 to 12) carbon atoms, more preferably a hydrogen atom or an alkyl group having 1 to 30 (preferably from 2 to 20, more preferably from 2 to 16, even more preferably from 2 to 12) carbon atoms, and even more preferably an alkyl group having 1 to 30 (preferably from 2 to 20, more preferably from 2 to 16, even more preferably from 2 to 12) carbon atoms.

From the viewpoint of realizing a pressure medium oil having a high solidification pressure at room temperature (25° C.), the pressure medium oil (A) that is one embodiment of the present invention preferably contains a compound represented by the following general formula (2A).

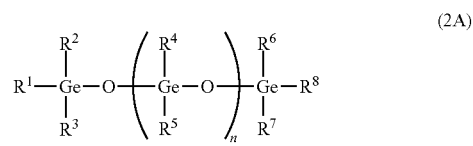

(2A)

In the general formula (2A), each of $R^1$ to $R^8$ independently represents a hydrogen atom, a halogen atom, an alkyl group or an alkoxy group, with the proviso that at least one of $R^1$ to $R^8$ is an alkyl group or an alkoxy group. n indicates an integer of 0 or more, preferably an integer of 1 or more, more preferably an integer of 2 to 30.

In the general formula (2A), $R^1$ to $R^8$ have the same meanings as those of $R^1$ to $R^8$ in the general formula (2), and for example, specific exemplified groups and the preferred carbon number of the selectable "alkyl group" and "alkoxy group" are the same as above.

In other words, preferably, each of $R^1$ to $R^8$ in the general formula (2A) independently represents a hydrogen atom, an alkyl group having 1 to 30 (preferably from 2 to 20, more preferably from 2 to 16, even more preferably from 2 to 12) carbon atoms, or an alkoxy group having 1 to 30 (preferably from 2 to 20, more preferably from 2 to 16, even more preferably from 2 to 12) carbon atoms, more preferably a hydrogen atom or an alkyl group having 1 to 30 (preferably from 2 to 20, more preferably from 2 to 16, even more preferably from 2 to 12) carbon atoms, and even more preferably an alkyl group having 1 to 30 (preferably from 2 to 20, more preferably from 2 to 16, even more preferably from 2 to 12) carbon atoms.

In the pressure medium oil (A) that is one embodiment of the present invention, the content of the compound represented by the general formula (1A) or (2A) is, based on the total amount (100% by mass) of the Group-14 element-containing organic compound in the pressure medium oil (A), preferably from 70 to 100% by mass, more preferably from 80 to 100% by mass, even more preferably from 90 to 100% by mass.

[Pressure Medium Oil (B)]

The pressure medium oil (B) that is one embodiment of the present invention contains an organic tin compound, but may further contain various additives within a range not detracting from the effects of the present invention.

In the pressure medium oil (B) that is one embodiment of the present invention, one type of organic tin compound may be used singly, or two or more types of organic tin compounds may be used in combination. The pressure medium oil (B) may contain, as the Group-14 element-containing organic compound therein, any other Group-14 element-containing organic compound than an organic tin compound, but the content of the other Group-14 element-containing organic compound than the organic tin compound is preferably not more than the content of the organic tin compound therein.

The content of the organic tin compound contained in the pressure medium oil (B) that is one embodiment of the present invention is, from the viewpoint of realizing a pressure medium oil having a high solidification pressure at room temperature (25° C.), preferably from 70 to 100% by mass based on the total amount (100% by mass) of the pressure medium oil (B), more preferably from 80 to 100% by mass, even more preferably from 85 to 100% by mass, still more preferably from 90 to 100% by mass, further more preferably from 95 to 100% by mass.

The organic tin compound contained in the pressure medium oil (B) is as mentioned above, but from the viewpoint of realizing a pressure medium oil having a high solidification pressure at room temperature (25° C.), preferably, a compound represented by the following general formula (1B) is contained.

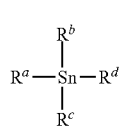

(1B)

In the general formula (1B), each of $R^a$, $R^b$, $R^c$, and $R^d$ independently represents a hydrogen atom, a halogen atom, an alkyl group or an alkoxy group, with the proviso that at least one of $R^a$, $R^b$, $R^c$, and $R^d$ is an alkyl group or an alkoxy group.

$R^a$ to $R^d$ in the general formula (1B) have the same meanings as those of $R^a$ to $R^d$ in the general formula (1), and for example, specific exemplified groups and the preferred carbon number of the selectable "alkyl group" and "alkoxy group" are the same as above.

In other words, preferably, each of $R^a$ to $R^d$ in the general formula (1B) independently represents a hydrogen atom, an alkyl group having 1 to 30 (preferably from 2 to 20, more preferably from 2 to 16, even more preferably from 2 to 12) carbon atoms, or an alkoxy group having 1 to 30 (preferably from 2 to 20, more preferably from 2 to 16, even more preferably from 2 to 12) carbon atoms, more preferably a hydrogen atom or an alkyl group having 1 to 30 (preferably from 2 to 20, more preferably from 2 to 16, even more preferably from 2 to 12) carbon atoms, and even more preferably an alkyl group having 1 to 30 (preferably from 2 to 20, more preferably from 2 to 16, even more preferably from 2 to 12) carbon atoms.

From the viewpoint of realizing a pressure medium oil having a high solidification pressure at room temperature (25° C.), the pressure medium oil (B) that is one embodiment of the present invention preferably contains a compound represented by the following general formula (2B).

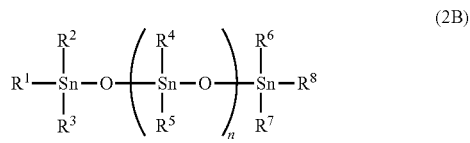

(2B)

In the general formula (2B), each of $R^1$ to $R^8$ independently represents a hydrogen atom, a halogen atom, an alkyl group or an alkoxy group, with the proviso that at least one of $R^1$ to $R^8$ is an alkyl group or an alkoxy group. n indicates an integer of 0 or more, preferably an integer of 1 or more, more preferably an integer of 2 to 30.

In the general formula (2B), $R^1$ to $R^8$ have the same meanings as those of $R^1$ to $R^8$ in the general formula (2), and for example, specific exemplified groups and the preferred carbon number of the selectable "alkyl group" and "alkoxy group" are the same as above.

In other words, preferably, each of $R^1$ to $R^8$ in the general formula (2B) independently represents a hydrogen atom, an alkyl group having 1 to 30 (preferably from 2 to 20, more preferably from 2 to 16, even more preferably from 2 to 12) carbon atoms, or an alkoxy group having 1 to 30 (preferably from 2 to 20, more preferably from 2 to 16, even more preferably from 2 to 12) carbon atoms, more preferably a hydrogen atom or an alkyl group having 1 to 30 (preferably from 2 to 20, more preferably from 2 to 16, even more preferably from 2 to 12) carbon atoms, and even more preferably an alkyl group having 1 to 30 (preferably from 2 to 20, more preferably from 2 to 16, even more preferably from 2 to 12) carbon atoms.

In the pressure medium oil (B) that is one embodiment of the present invention, the content of the compound represented by the general formula (1B) or (2B) is, based on the total amount (100% by mass) of the Group-14 element-containing organic compound in the pressure medium oil (B), preferably from 70 to 100% by mass, more preferably from 80 to 100% by mass, even more preferably from 90 to 100% by mass.

[Pressure Medium Oil (C)]

The pressure medium oil (C) that is one embodiment of the present invention contains an organic lead compound, but may further contain various additives within a range not detracting from the effects of the present invention.

In the pressure medium oil (C) that is one embodiment of the present invention, one type of organic lead compound may be used singly, or two or more types of organic lead compounds may be used in combination. The pressure medium oil (C) may contain, as the Group-14 element-containing organic compound therein, any other Group-14 element-containing organic compound than an organic lead compound, but the content of the other Group-14 element-containing organic compound than the organic lead compound is preferably not more than the content of the organic lead compound therein.

The content of the organic lead compound contained in the pressure medium oil (C) that is one embodiment of the present invention is, from the viewpoint of realizing a pressure medium oil having a high solidification pressure at room temperature (25° C.), preferably from 70 to 100% by mass based on the total amount (100% by mass) of the pressure medium oil (C), more preferably from 80 to 100% by mass, even more preferably from 85 to 100% by mass, still more preferably from 90 to 100% by mass, further more preferably from 95 to 100% by mass.

The organic lead compound contained in the pressure medium oil (C) is as mentioned above, but from the viewpoint of realizing a pressure medium oil having a high solidification pressure at room temperature (25° C.), preferably, a compound represented by the following general formula (1C) is contained.

(1C)

In the general formula (1C), each of $R^a$, $R^b$, $R^c$, and $R^d$ independently represents a hydrogen atom, a halogen atom, an alkyl group or an alkoxy group, with the proviso that at least one of $R^a$, $R^b$, $R^c$, and $R^d$ is an alkyl group or an alkoxy group.

$R^a$ to $R^d$ in the general formula (1C) have the same meanings as those of $R^a$ to $R^d$ in the general formula (1), and for example, specific exemplified groups and the preferred carbon number of the selectable "alkyl group" and "alkoxy group" are the same as above.

In other words, preferably, each of $R^a$ to $R^d$ in the general formula (1C) independently represents a hydrogen atom, an alkyl group having 1 to 30 (preferably from 2 to 20, more preferably from 2 to 16, even more preferably from 2 to 12) carbon atoms, or an alkoxy group having 1 to 30 (preferably from 2 to 20, more preferably from 2 to 16, even more preferably from 2 to 12) carbon atoms, more preferably a hydrogen atom or an alkyl group having 1 to 30 (preferably from 2 to 20, more preferably from 2 to 16, even more preferably from 2 to 12) carbon atoms, and even more preferably an alkyl group having 1 to 30 (preferably from 2 to 20, more preferably from 2 to 16, even more preferably from 2 to 12) carbon atoms.

From the viewpoint of realizing a pressure medium oil having a high solidification pressure at room temperature (25° C.), the pressure medium oil (C) that is one embodiment of the present invention preferably contains a compound represented by the following general formula (2C).

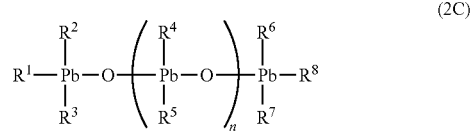

(2C)

In the general formula (2C), each of $R^1$ to $R^8$ independently represents a hydrogen atom, a halogen atom, an alkyl group or an alkoxy group, with the proviso that at least one of $R^1$ to $R^8$ is an alkyl group or an alkoxy group. n indicates an integer of 0 or more, preferably an integer of 1 or more, more preferably an integer of 2 to 30.

In the general formula (2C), $R^1$ to $R^8$ have the same meanings as those of $R^1$ to $R^8$ in the general formula (2), and for example, specific exemplified groups and the preferred carbon number of the selectable "alkyl group" and "alkoxy group" are the same as above.

In other words, preferably, each of $R^1$ to $R^8$ in the general formula (2C) independently represents a hydrogen atom, an alkyl group having 1 to 30 (preferably from 2 to 20, more preferably from 2 to 16, even more preferably from 2 to 12) carbon atoms, or an alkoxy group having 1 to 30 (preferably from 2 to 20, more preferably from 2 to 16, even more preferably from 2 to 12) carbon atoms, more preferably a hydrogen atom or an alkyl group having 1 to 30 (preferably from 2 to 20, more preferably from 2 to 16, even more preferably from 2 to 12) carbon atoms, and even more preferably an alkyl group having 1 to 30 (preferably from 2 to 20, more preferably from 2 to 16, even more preferably from 2 to 12) carbon atoms.

In the pressure medium oil (C) that is one embodiment of the present invention, the content of the compound represented by the general formula (1C) or (2C) is, based on the total amount (100% by mass) of the Group-14 element-containing organic compound in the pressure medium oil (C), preferably from 70 to 100% by mass, more preferably from 80 to 100% by mass, even more preferably from 90 to 100% by mass.

<Various Additives and Others>

As various additives to be contained in the pressure medium oil of one embodiment of the present invention, for example, there are mentioned antioxidants such as amine-type ones, phenolic ones, etc.; corrosion inhibitors such as benzotriazole-type ones, thiazole-type ones, etc.; rust inhibitors such as metal sulfonate-type ones, succinate-types ones, etc.; defoaming agents such as silicone-type ones, fluoro-silicone-type ones, etc.; viscosity index improvers such as polymethacrylate-type ones, olefin copolymer-type ones, etc.

The total content of such various additives is, based on the total amount (100% by mass) of the pressure medium oil, preferably from 0.01 to 20% by mass, more preferably from 0.05 to 15% by mass, even more preferably from 0.1 to 10% by mass.

The pressure medium oil of one embodiment of the present invention may contain impurities such as the starting material compounds and the side products, which may form in synthesis of the above-mentioned Group-14 element-containing organic compound selected from the organic germanium compound, the organic tin compound, and the organic lead compound, as well as the degradation products of the Group-14 element-containing organic compound selected from the organic germanium compound, the organic tin compound, and the organic lead compound, which may form during use of the pressure medium oil, within a range not detracting from the effects of the present invention.

The content of the impurities in the pressure medium oil of one embodiment of the present invention is, based on the total amount (100% by mass) of the pressure medium oil, preferably 5% by mass or less, more preferably 1% by mass or less, even more preferably 0.1% by mass or less.

[Various Physical Properties of Pressure Medium Oil of the Invention]

The solidification pressure at 25° C. of the pressure medium oil of one embodiment of the present invention is preferably more than 3.7 GPa, more preferably 3.9 GPa or more, even more preferably 4.05 GPa or more.

The solidification pressure of the pressure medium oil of one embodiment of the present invention may be more than 3.7 GPa, and therefore the pressure medium oil does not solidify even under an ultrahigh pressure of more than 3.7 GPa, and can apply a pressure uniformly to an object substance to be pressurized.

In the present invention, the solidification pressure at 25° C. of the pressure medium oil means the value measured according to the method described in the section of Examples.

The kinematic viscosity at 40° C. of the pressure medium oil of one embodiment of the present invention is preferably 20 mm²/s or less.

The kinematic viscosity at 100° C. of the pressure medium oil of one embodiment of the present invention is preferably from 0.1 to 10 mm²/s.

The pour point of the pressure medium oil of one embodiment of the present invention is, from the viewpoint of realizing a pressure medium oil that does not solidify at a low temperature and that can be used in low-temperature experiments, preferably −40° C. or lower, more preferably −45° C. or lower, even more preferably lower than −50° C.

The pressure medium oil of the present invention can be a pressure medium oil having characteristics of not solidifying even under an ultrahigh pressure higher than 3.7 GPa at room temperature (25° C.), having a low pour point, and hardly dissolving a conductive paste.

Consequently, the pressure medium oil of one embodiment of the present invention is favorable as a pressure medium oil for pressure application systems, which is used in a pressure application system for applying a pressure to a substance.

The present invention also provides a method of using a pressure medium oil for applying a pressure to a substance via the pressure medium oil of the present invention.

In the method of using a pressure medium oil of one embodiment of the present invention, the maximum value of the pressure to be applied to a substance is preferably more than 3.7 GPa, more preferably 3.9 GPa or more, even more preferably 4.05 GPa or more.

In the method of using a pressure medium oil of one embodiment of the present invention, it is naturally possible to apply a pressure not higher than the above-mentioned maximum value of the pressure to a substance.

EXAMPLES

Next, the present invention is described in more detail with reference to Examples; however, the present invention is not whatsoever restricted by these Examples.

Examples 1 to 2 and Comparative Examples 1 to 3

Regarding the pressure medium oil consisting any of the following compounds, various physical properties thereof of the following (1) to (6) were measured or evaluated. The results are shown in Table 1.

Example 1

Tetrabutyl germanium (organic germanium compound of the general formula (1A) where $R^a$ to $R^d$ are "n-butyl group").

Example 2

Tetrabutyl tin (organic tin compound of the general formula (1B) where $R^a$ to $R^d$ are "n-butyl group").

Comparative Example 1: Diethyldioctyl Silane

Comparative Example 2: Hexyldimethyloctyl Silane

Comparative Example 3: Poly-α-olefin

[Method for Measurement or Evaluation of Various Physical Properties]
(1) Kinematic Viscosity at 40° C. or 100° C.
Measured according to the method of JIS K 2283.
(2) Density
Measured according to the method of JIS K 2249 in an environment at 15° C.
(3) Pour Point
Measured according to the method of JIS K 2269.
(4) Solidification Pressure at 25° C.
In an environment at 25° C., a strain gauge was put in a pressure container formed in a cubic form, and the pressure container was filled with a pressure medium oil. For applying an ultrahigh pressure, the pressure container was pressurized in 6 directions, and the resistance value of the strain gauge at this time was measured. The relationship between the pressure and the resistance value was graphed, and on the resulting graph, the point at which the curve of the resistance value relative to the pressure folds discontinuously is identified as a solidification pressure point.

The strain gauge is a tabular measurement device, and when compressed more, the resistance value lowers. When the pressure medium oil is a liquid, the entire device is uniformly compressed and contracted, and the compression of the device can be detected, but contrary to this, when pressurized via a solidified pressure medium oil, the compression of the solidified pressure medium oil is detected and therefore, the compression ratio of the strain gauge is increased, so that the resistance value is decreased rapidly across the solidification pressure point border. Consequently, in the graph of the relationship of the pressure and the resistance value, a point at which the curve of the resistance value relative to the pressure folds appears, and the point is identified as "solidification pressure point".

In the case where temperature control at 25° C. is difficult, the sample may be analyzed at two temperatures near 25° C. (temperature lower than 25° C. and temperature higher than 25° C.), and as a linear interpolation value, the solidification pressure at 25° C. may be calculated.
(5) Presence or Absence of Dissolution of Conductive Paste
In visual inspection and electric measurement using a conductive paste, there occurred no trouble and, as a result, no dissolution of the conductive paste was confirmed.

TABLE 1

|  |  | Example 1 | Example 2 | Comparative Example 1 | Comparative Example 2 | Comparative Example 3 |
|---|---|---|---|---|---|---|
| Constituent compound in pressure medium oil |  | Tetrabutyl germanium | Tetrabutyl tin | Diethyldioctyl silane | Hexyldimethyloctyl silane | Poly-α-olefin |
| Evaluation items | unit |  |  |  |  |  |
| Kinematic viscosity (40° C.) | mm²/s | 2.186 | 1.689 | 4.373 | 2.69 | 17.5 |
| Kinematic viscosity (100° C.) | mm²/s | 0.908 | 0.808 | 1.604 | 1.125 | 3.9 |
| Density (15° C.) | g/cm³ | 0.9343 | 1.0534 | 0.8117 | 0.7911 | 0.819 |

TABLE 1-continued

|  |  | Example 1 | Example 2 | Comparative Example 1 | Comparative Example 2 | Comparative Example 3 |
|---|---|---|---|---|---|---|
| Pour point | ° C. | Lower than −50 | Lower than −50 | Lower than −50 | Lower than −50 | Lower than −50 |
| Solidification pressure (25° C.) | GPa | 4.05 | 4.07 | 3.7 | 3.2 | 2.3 |
| Dissolution of conductive paste | — | no | no | no | no | no |

As in Table 1, the pressure medium oils of Examples 1 and 2 had an extremely high solidification pressure value at 25° C. as compared with the pressure medium oils of Comparative Examples 1 to 3.

INDUSTRIAL APPLICABILITY

The pressure medium oil of the present invention is favorable as a pressure medium oil to be used in pressure application systems and the like for applying a high pressure higher than at most 3.7 GPa to a substance.

The invention claimed is:

1. A method, comprising applying pressure to a substance with a pressure medium oil comprising a Group-14 element-containing organic compound selected from the group consisting of an organic germanium compound, an organic tin compound, and an organic lead compound, wherein:
a content of the Group-14 element-containing organic compound is from 70 to 100% by mass, based on a total amount of the pressure medium oil;
a kinematic viscosity at 40° C. of the Group-14 element-containing organic compound is 20 mm²/s or less; and
the pour point of the Group-14 element-containing organic compound is −40° C. or lower, or
the pressure medium oil has a solidification pressure at 25° C. of more than 3.7 GPa.

2. The method according to claim 1, wherein the pour point of the Group-14 element-containing organic compound is −40° C. or lower.

3. The method according to claim 1, wherein the content of the Group-14 element-containing organic compound is from 80 to 100% by mass, based on the total amount of the pressure medium oil.

4. A method, comprising applying pressure to a substance with a pressure medium oil comprising a Group-14 element-containing organic compound selected from the group consisting of an organic germanium compound, an organic tin compound, and an organic lead compound, wherein the Group-14 element-containing organic compound comprises a compound represented by the following general formula (1) or a compound represented by the following general formula (2):

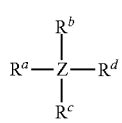
(1)

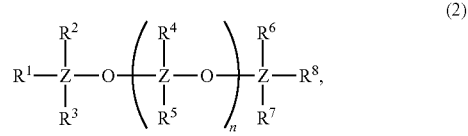
(2)

wherein:
a content of the Group-14 element-containing organic compound is from 70 to 100% by mass, based on a total amount of the pressure medium oil;
a kinematic viscosity at 40° C. of the Group-14 element-containing organic compound is 20 mm²/s or less;
each of $R^a$, $R^b$, $R^c$, and $R^d$ independently represents a hydrogen atom, a halogen atom, an alkyl group, or an alkoxy group, with the proviso that at least one of $R^a$, $R^b$, $R^c$, and $R^d$ is an alkyl group or an alkoxy group;
each of $R^1$ to $R^8$ independently represents a hydrogen atom, a halogen atom, an alkyl group or an alkoxy group, with the proviso that at least one of $R^1$ to $R^8$ is an alkyl group or an alkoxy group;
n indicates an integer of 0 or more; and
each of Z independently represents a germanium atom, a tin atom or a lead atom, and plural Z's may be the same as or different from each other.

5. The method according to claim 4, wherein:
the Group-14 element-containing organic compound comprises the compound represented by the following general formula (1); and
each of $R^a$, $R^b$, $R^c$, and $R^d$ in the general formula (1) independently represents a hydrogen atom, an alkyl group having 1 to 30 carbon atoms, or an alkoxy group having 1 to 30 carbon atoms.

6. The method according to claim 4, wherein:
the Group-14 element-containing organic compound comprises the compound represented by the general formula (2)
each of $R^1$ to $R^8$ independently represents a hydrogen atom, a halogen atom, an alkyl group or an alkoxy group, with the proviso that at least one of $R^1$ to $R^8$ is an alkyl group or an alkoxy group;
n indicates an integer of 0 or more; and
each of Z independently represents a germanium atom, a tin atom or a lead atom, and plural Z's may be the same as or different from each other.

7. A method, comprising applying pressure to a substance with a pressure medium oil comprising an organic germanium compound comprising a compound represented by the following general formula (1A) or a compound represented by the following general formula (2A):

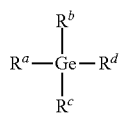

(1A)

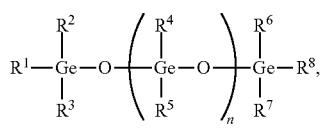

(2A)

wherein:
a content of the Group-14 element-containing organic compound is from 70 to 100% by mass, based on a total amount of the pressure medium oil;
a kinematic viscosity at 40° C. of the Group-14 element-containing organic compound is 20 mm$^2$/s or less;
each of $R^a$, $R^b$, $R^c$, and $R^d$ independently represents a hydrogen atom, a halogen atom, an alkyl group or an alkoxy group, with the proviso that at least one of $R^a$, $R^b$, $R^c$, and $R^d$ is an alkyl group or an alkoxy group;
each of $R^1$ to $R^8$ independently represents a hydrogen atom, a halogen atom, an alkyl group or an alkoxy group, with the proviso that at least one of $R^1$ to $R^8$ is an alkyl group or an alkoxy group; and
n indicates an integer of 0 or more.

8. The method according to claim 7, wherein:
the organic germanium compound comprises the compound represented by the general formula (2A)
each of $R^1$ to $R^8$ independently represents a hydrogen atom, a halogen atom, an alkyl group or an alkoxy group, with the proviso that at least one of $R^1$ to $R^8$ is an alkyl group or an alkoxy group; and
n indicates an integer of 0 or more.

9. A method, comprising applying pressure to a substance with a pressure medium oil comprising an organic tin compound comprising a compound represented by the following general formula (1B) or a compound represented by the following general formula (2B):

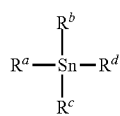

(1B)

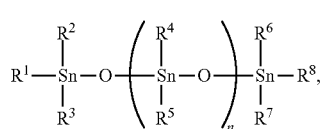

(2B)

wherein:
a content of the Group-14 element-containing organic compound is from 70 to 100% by mass, based on a total amount of the pressure medium oil;
a kinematic viscosity at 40° C. of the Group-14 element-containing organic compound is 20 mm$^2$/s or less;
each of $R^a$, $R^b$, $R^c$, and $R^d$ independently represents a hydrogen atom, a halogen atom, an alkyl group, or an alkoxy group, with the proviso that at least one of $R^a$, $R^b$, $R^c$, and $R^d$ is an alkyl group or an alkoxy group;
each of $R^1$ to $R^8$ independently represents a hydrogen atom, a halogen atom, an alkyl group or an alkoxy group, with the proviso that at least one of $R^1$ to $R^8$ is an alkyl group or an alkoxy group; and
n indicates an integer of 0 or more.

10. The method according to claim 9, wherein the organic tin compound comprises the compound represented by the general formula (2B)
wherein:
each of $R^1$ to $R^8$ independently represents a hydrogen atom, a halogen atom, an alkyl group or an alkoxy group, with the proviso that at least one of $R^1$ to $R^8$ is an alkyl group or an alkoxy group; and
n indicates an integer of 0 or more.

11. A method, comprising applying pressure to a substance with a pressure medium oil comprising an organic lead compound comprising a compound represented by the following general formula (1C) or a compound represented by the following general formula (2C):

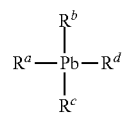

(1C)

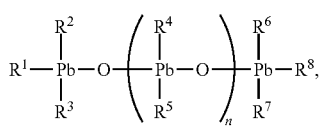

(2C)

wherein:
a content of the Group-14 element-containing organic compound is from 70 to 100% by mass, based on a total amount of the pressure medium oil;
a kinematic viscosity at 40° C. of the Group-14 element-containing organic compound is 20 mm$^2$/s or less;
each of $R^a$, $R^b$, $R^c$, and $R^d$ independently represents a hydrogen atom, a halogen atom, an alkyl group, or an alkoxy group, with the proviso that at least one of $R^a$, $R^b$, $R^c$, and $R^d$ is an alkyl group or an alkoxy group;
each of $R^1$ to $R^8$ independently represents a hydrogen atom, a halogen atom, an alkyl group or an alkoxy group, with the proviso that at least one of $R^1$ to $R^8$ is an alkyl group or an alkoxy group; and
n indicates an integer of 0 or more.

12. The method according to claim 1, wherein the organic lead compound comprises the compound represented by the general formula (2C)
wherein:
each of $R^1$ to $R^8$ independently represents a hydrogen atom, a halogen atom, an alkyl group or an alkoxy group, with the proviso that at least one of $R^1$ to $R^8$ is an alkyl group or an alkoxy group; and
n indicates an integer of 0 or more.

13. The method according to claim 1, wherein the pressure medium oil has a solidification pressure at 25° C. of more than 3.7 GPa.

14. The method according to claim 4, wherein the Group-14 element-containing organic compound comprises the compound represented by the general formula (1).

15. The method according to claim 7, wherein the organic germanium compound comprises the compound represented by the general formula (1A).

16. The method according to claim 9, wherein the organic tin compound comprises the compound represented by the general formula (1B).

17. The method according to claim 11, wherein the organic lead compound comprises the compound represented by the general formula (1C).

* * * * *